US009957266B2

(12) United States Patent
Gobbi et al.

(10) Patent No.: US 9,957,266 B2
(45) Date of Patent: May 1, 2018

(54) IMIDAZO[1,2-A]PYRIDIN-7-AMINE

(71) Applicant: Hoffmann-La Roche Inc., Little Falls, NJ (US)

(72) Inventors: Luca Gobbi, Buus (CH); Henner Knust, Rheinfelden (DE); Matthias Koerner, Grenzach-Wyhlen (DE); Dieter Muri, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 132 days.

(21) Appl. No.: 15/081,002

(22) Filed: Mar. 25, 2016

(65) Prior Publication Data

US 2016/0207919 A1    Jul. 21, 2016

Related U.S. Application Data

(63) Continuation of application No. PCT/EP2014/070162, filed on Sep. 23, 2014.

(30) Foreign Application Priority Data

Sep. 26, 2013  (EP) ..................................... 13186074

(51) Int. Cl.
| *A61K 51/00* | (2006.01) |
| *A61M 36/14* | (2006.01) |
| *C07D 471/04* | (2006.01) |
| *A61K 49/00* | (2006.01) |
| *A61K 51/04* | (2006.01) |

(52) U.S. Cl.
CPC ............ *C07D 471/04* (2013.01); *A61K 49/00* (2013.01); *A61K 51/0455* (2013.01)

(58) Field of Classification Search
CPC .... A61K 49/00; A61K 51/00; A61K 51/0455; A61K 2300/00; A61K 2121/00; A61K 2123/00; C07D 235/04; C07D 233/02; C07D 233/04; C07D 233/54; C07D 471/04
USPC .... 424/1.11, 1.65, 1.81, 1.85, 1.89, 9.1, 9.2, 424/9.3, 9.4, 9.5, 9.6; 548/300.1, 304.4, 548/335.1, 347.1
See application file for complete search history.

(56) References Cited

U.S. PATENT DOCUMENTS

2002/0188000 A1* 12/2002 Crawforth ............ A61K 31/437
514/291

FOREIGN PATENT DOCUMENTS

| EP | 1956013 A1 | 8/2008 |
| EP | 2 264 018 A2 | 12/2010 |
| JP | 2005-512945 A | 5/2005 |
| JP | 2006-522104 A | 9/2006 |
| JP | 2008-546804 A | 12/2008 |
| JP | 2012-502966 A | 2/2012 |
| WO | 03/018070 A1 | 3/2003 |
| WO | 2007/002540 A2 | 1/2007 |
| WO | 2009/004914 A1 | 1/2009 |
| WO | 2009/057576 A1 | 7/2009 |
| WO | 2010/034982 A1 | 4/2010 |
| WO | 2014/177458 A1 | 11/2014 |

OTHER PUBLICATIONS

ISR for PCT/EP2014/070162 (dated Oct. 27, 2014).

* cited by examiner

*Primary Examiner* — D L Jones
(74) *Attorney, Agent, or Firm* — Tamara A. Kale

(57) ABSTRACT

The present invention relates to compounds that may be used for binding and imaging tau aggregates and related beta-sheet aggregates including, for example, beta-amyloid aggregates or alpha-synuclein aggregates.

11 Claims, 1 Drawing Sheet

Figure 1
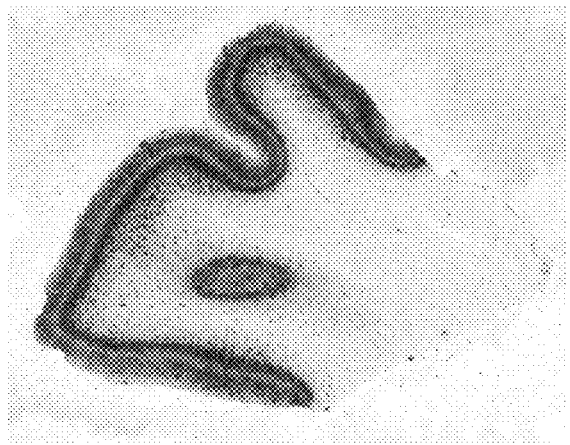
Figure 2
Figure 3

IMIDAZO[1,2-A]PYRIDIN-7-AMINE

This application is a continuation of International Application No. PCT/EP2014/070162, filed Sep. 23, 2014, which claims priority to European Application No. 13186074.4, filed Sep. 26, 2013, each of which is incorporated herein by reference in its entirety.

The present invention relates to compounds of general formula

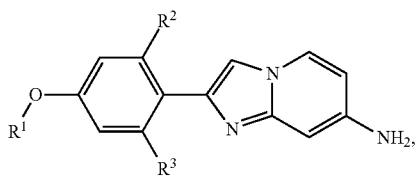

I wherein
$R^1$ is lower alkyl or lower alkyl substituted by halogen;
$R^2$, $R^3$ are hydrogen or tritium;
or to a pharmaceutically acceptable acid addition salt.

Similar compounds are described for example in WO2011/117264 as modulators of phosphodiesterase 10A (PDE10A) for the treatment of central nervous system diseases and in WO2010/068453 and WO2010/068452 as modulators of fatty acid amide hydrolase. 2-Aryl-3-(heteroaryl)-imidazo(1,2-a)pyrimidines are described in WO0134605 for the treatment of conditions alleviated by the reduction of inflammatory cytokines.

It has been shown that the present compounds may be used for binding and imaging tau aggregates and related beta-sheet aggregates including besides others beta-amyloid aggregates or alpha-synuclein aggregates, especially for use in binding and imaging tau aggregates in Alzheimer patients.

Alzheimer's disease (AD) is a progressive neurodegenerative disorder characterized by cognitive decline, irreversible memory loss, disorientation and language impairment (Arch. Neurol. 1985, 42(11), 1097-1105). Postmortem examination of AD brain sections reveals abundant senile plaques (SPs), composed of beta amyloid (Aβ) peptides, and numerous neurofibrillary tangles (NFTs) formed by filaments of hyperphosphorylated tau protein.

Tau belongs to the family of microtubule-associated proteins and is mainly expressed in neurons where it plays an important role in the assembly of tubulin monomers into microtubules to constitute the neuronal microtubule network as tracks for axonal transport (Brain Res. Rev. 2000, 33(1), 95-130). Tau is translated from a single gene located on chromosome 17 and the expression is developmentally regulated by an alternative splicing mechanism generating six different isoforms in the human adult brain that can be distinguished by their number of binding domains. The underlying mechanisms leading to tau hyperphosphorylation, misfolding and aggregation are not well understood, but the deposition of tau aggregates follows a stereotyped spatiotemporal pathway both at the intracellular levels as well as on the level of brain topography.

The recent discovery of tau gene mutations leading to frontotemporal dementia (FTD) with parkinsonism linked to chromosome 17 has reinforced the predominant role attributed to tau in the pathogenesis of neurodegenerative disorders and underlined the fact that distinct sets of tau isoforms expressed in different neuronal populations could lead to different pathologies (Biochim. Biophys. Acta 2005, 1739 (2) 240-250). Neurodegenerative diseases characterized by pathological tau accumulation are termed 'tauopathies' (Ann. Rev. Neurosci. 2001, 24, 1121-1159). Besides AD and FTD, other tauopathies include progressive supranuclear palsy (PSP), tangle-predominant dementia, Pick's disease, frontotemporal lobar degeneration (FTLD), Down's syndrome and others.

A direct correlation has been established between the progressive involvement of neocortical areas and the increasing severity of dementia, suggesting that pathological tau aggregates such as NFTs are a reliable marker of the neurodegenerative process. The degree of NFT involvement in AD is defined by Braak stages (Acta Neuropathol. 1991, 82, 239-259). Braak stages I and II are defined when NFT involvement is confined mainly to the transentorhinal region of the brain, stages III and IV are diagnosed when limbic regions such as the hippocampus are involved, and stages V and VI when extensive neocortical involvement is found.

Presently, detection of tau aggregates is only possible by histological analysis of biopsy or autopsy materials. In vivo imaging of tau pathology would provide novel insights into deposition of tau aggregates in the human brain and allow to non-invasively examine the degree of tau pathology, quantify changes in tau deposition over time, assess its correlation with cognition and analyze the efficacy of an anti-tau therapy. Potential ligands for detecting tau aggregates in the living brain must cross the blood-brain barrier and possess high affinity and specificity for tau aggregates. To this end, successful neuroimaging radiotracers must have appropriate lipophilicity (log D 1-3) and low molecular weight (<450), show rapid clearance from blood and low non-specific binding.

The object of the present application is to find an imaging tool which will improve diagnosis by identifying potential patients with excess of tau aggregates in the brain, which may be likely to develop Alzheimer's disease. It will also be useful to monitor the progression of the disease. When an anti-tau aggregate drug becomes available, imaging tau tangles in the brain may provide an essential tool for monitoring treatment.

A further object of the present invention is a method of imaging tau-aggregate deposits, comprising
 introducing into a mammal a detectable quantity of a composition
 allowing sufficient time for the compound of formula I to be associated with tau-aggregate deposits, and
 detecting the compound associated with one or more tau-aggregate deposits.

A further object of the present invention is a pharmaceutical composition, containing compounds of formula I and pharmaceutical acceptable carriers, which may be used for identifying potential patients.

BRIEF DESCRIPTION OF THE FIGURES

FIG. 1 is an autoradiogram of [$^3$H]-2-(4-methoxyphenyl)imidazo[1,2-a]pyridin-7-amine (example 5) incubated with human cortical brain sections obtained from a Braak V staged AD patient. The radioligand concentration was 2.6 nM.

FIG. 2 is an autoradiogram of [$^3$H]-2-[4-(2-fluoroethoxy)phenyl]imidazo[1,2-a]pyridin-7-amine (example 6) incubated with human cortical brain sections obtained from a Braak V staged AD patient. The radioligand concentration was 2.5 nM.

FIG. 3 represents data from the TAU radioligand in vitro displacement assay described below. This in vitro binding assay assesses the affinity of compounds for native tau aggregates. The compounds are co-incubated with the well-established tau specific radioligand [$^3$H]T808 and the compound's displacement potency of [$^3$H]T808 binding is determined by in vitro autoradiography using human Alzheimer's disease (AD) brain sections.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, and isopropyl.

The term "halogen" denotes chlorine, bromine, fluorine or iodine.

The term "lower alkyl substituted by halogen" denotes an alkyl group as defined above, wherein at least one hydrogen atom is replaced by a halogen atom.

$^3$H denotes a tritium atom.

The term "leaving group" denotes halogen or sulfonate. Examples of sulfonate are tosylate, mesylate, triflate, nosylate or brosylate.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

It has been found that the compounds of formula I may be used for binding and imaging tau aggregates and related beta-sheet aggregates including besides others beta-amyloid aggregates or alpha-synuclein aggregates.

One embodiment of the present invention are compounds of formula I wherein R$^1$ is lower alkyl, for example the following compounds
2-(4-methoxyphenyl)imidazo[1,2-a]pyridin-7-amine
[$^3$H]-2-(4-methoxyphenyl)imidazo[1,2-a]pyridin-7-amine.

One embodiment of the present invention are further compounds of formula I wherein R$^1$ is lower alkyl substituted by halogen, for example the following compounds
2-(4-(fluoromethoxy)phenyl)imidazo[1,2-a]pyridin-7-amine
2-[4-(3-fluoropropoxy)phenyl]imidazo[1,2-a]pyridin-7-amine
2-[4-(2-fluoroethoxy)phenyl]imidazo[1,2-a]pyridin-7-amine
[$^3$H]-2-[4-(2-fluoroethoxy)phenyl]imidazo[1,2-a]pyridin-7-amine.

One embodiment of the present invention are further compounds of formula I wherein R$^2$ and R$^3$ are tritium, for example the following compounds
[$^3$H]-2-(4-methoxyphenyl)imidazo[1,2-a]pyridin-7-amine
[$^3$H]-2-[4-(2-fluoroethoxy)phenyl]imidazo[1,2-a]pyridin-7-amine.

The compounds of formula I may be used in binding and imaging tau aggregates, beta-amyloid aggregates, alpha-synuclein aggregates or huntingtin aggregates.
The preferred use of compounds of formula I is the use in binding and imaging tau aggregates in Alzheimer patients.

Furthermore, the compounds of formula I may be used in a tau-binding study.

The compounds of formula I are suitable for diagnostic imaging of tau-aggregates in the brain of a mammal.

The invention is also used for diagnostic imaging of tau-aggregate deposits in the brain of a mammal.

The present compounds of formula I

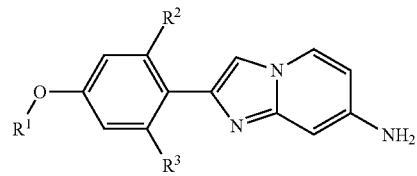

and their pharmaceutically acceptable salts can be prepared by processes described below, which process comprises
a) Amination of a Compound of Formula 2 (X=Cl, Br)

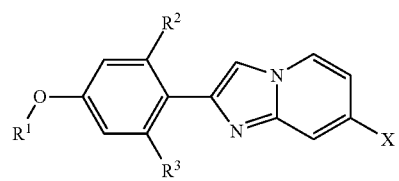

with NH$_4$OH
to afford a compound of formula I

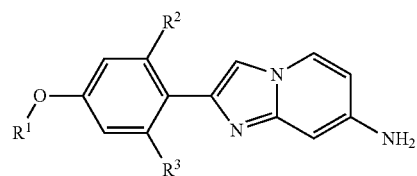

wherein R$^1$ is as defined above, and R$^2$ and R$^3$ are hydrogen, and, if desired, converting the compounds obtained into pharmaceutically acceptable acid addition salts, or
b) Coupling a Compound of Formula 4

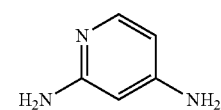

with a corresponding α-activated ketone of formula 3 (X is a leaving group, e.g. Br)

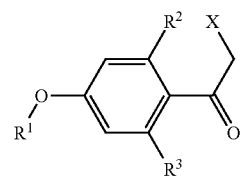

to afford a compound of formula I

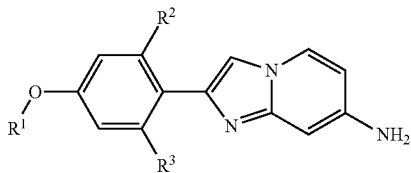

wherein R¹ is as defined above, and R² and R³ are hydrogen, and, if desired, converting the compounds obtained into pharmaceutically acceptable acid addition salts, or c) Reacting a Compound of Formula 5

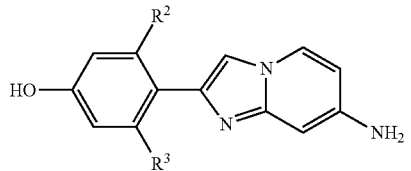

with a suitable alkylation agent R¹—X (X is halogen or sulfonate)
to afford a compound of formula I

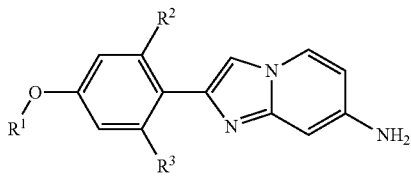

wherein R¹ is as defined above, and R² and R³ are hydrogen, and, if desired, converting the compounds obtained into pharmaceutically acceptable acid addition salts, and d) Reacting a Compound of Formula I

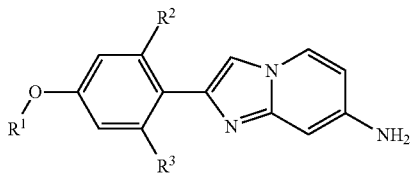

wherein R² and R³ are hydrogen,
with tritium gas in the presence of a catalyst, e.g. iridium, ruthenium, rhodium or palladium containing complexes in a suitable solvent, e.g. dichloromethane, chlorobenzene, DMF, DMSO or mixtures thereof at ambient or elevated temperature
to afford compound of formula I

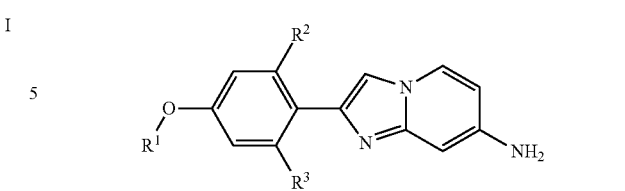

wherein R¹ is as defined above and R² and R³ are tritium, and, if desired, converting the compounds obtained into pharmaceutically acceptable acid addition salts.

The following schemes 1-3 describe the processes for the preparation of compounds of formula I in more detail.

The preparation of compounds of formula I of the present invention may be carried out in sequential or convergent synthetic routes. The skills required for carrying out the reactions and purifications of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the ones displayed in schemes 1 to 3, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

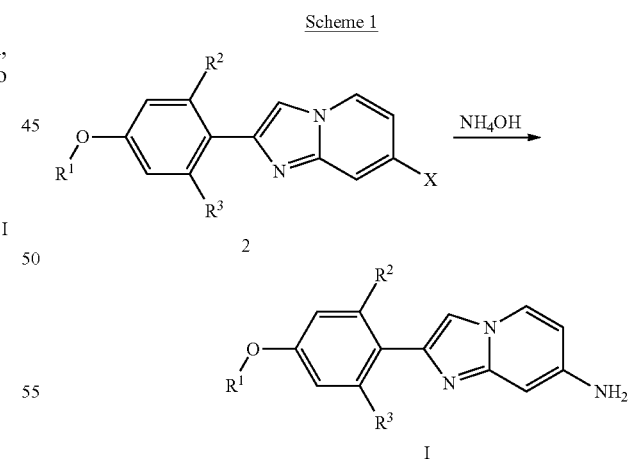

According to scheme 1, derivatives of imidazopyridine I, wherein the substituent R¹ is as defined above and R² and R³ are hydrogen, are prepared via an amination reaction of compound of formula 2 with a suitable ammonia reagent, e.g. ammonium hydroxide, in the presence of a suitable catalyst, e.g. copper(I) oxide, in a suitable solvent, e.g. N-methyl-2-pyrrolidinone at elevated or ambient temperature.

Scheme 2

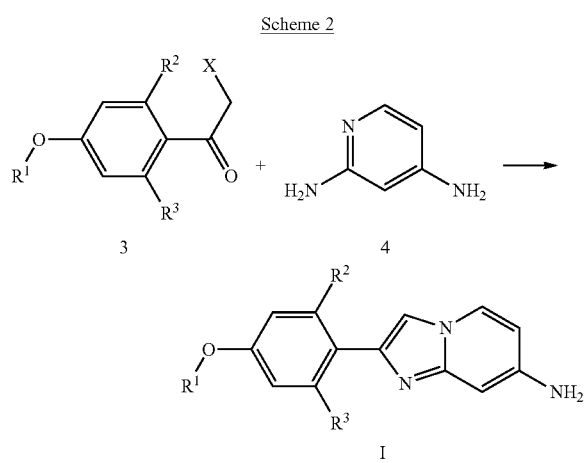

According to scheme 2, an activated ketone 3, wherein the substituent $R^1$ is as defined above, $R^2$ and $R^3$ are hydrogen and X is halogen, is reacted with amino-pyridine 4 in a suitable solvent, e.g. acetone or ethanol, at elevated temperature in an oil bath or in a microwave reactor to afford derivatives of compound I.

Scheme 3

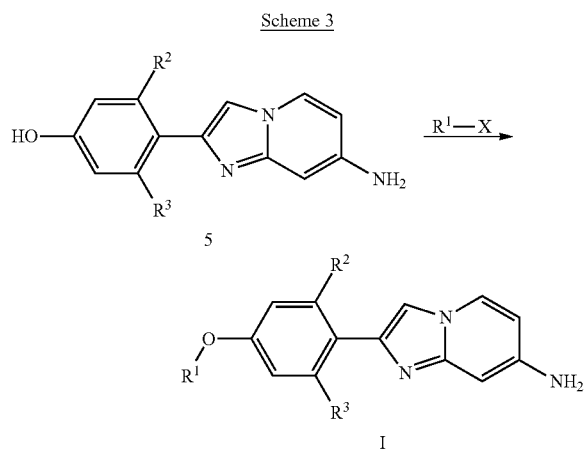

According to scheme 3, further derivatives of imidazopyridines I, wherein the substituent $R^1$ is as defined above, are synthesized by alkylation of phenols 5 using a suitable alkylation reagent $R^1$—X, e.g. alkyl halogenide like 1-fluoroethyl bromide or alkyl tosylate like fluoromethyl tosylate, in presence of a suitable base, e.g. cesium carbonate or sodium hydride, in a suitable solvent, e.g. DMF, at ambient or elevated temperature.

Isolation and Purification of the Compounds

Isolation and purification of the compounds and intermediates described herein can be achieved, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be found by reference to the preparations and examples herein below. However, other equivalent separation or isolation procedures could, of course, also be used.

Salts of Compounds of Formula I

The compounds of formula I are basic and may be converted to a corresponding acid addition salt. The conversion is accomplished by treatment with at least a stoichiometric amount of an appropriate inorganic acid, such as hydrochloric acid, hydrobromic acid, sulfuric acid, nitric acid, phosphoric acid and the like, or an organic acid such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid is added in a similar solvent. The temperature is maintained between 0° C. and 50° C. The resulting salt precipitates spontaneously or may be precipitated by addition of a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like. The compounds were investigated in accordance with the test given hereinafter.

TAU Radioligand-In-Vitro Displacement Assay

This in vitro binding assay assesses the affinity of compounds for native tau aggregates. The compounds are co-incubated with the well-established tau specific radioligand [$^3$H]T808 and the compound's displacement potency of [$^3$H]T808 binding is determined by in vitro autoradiography using human Alzheimer's disease (AD) brain sections (see FIG. 3).

Materials

AD human brains are purchased from Banner Sun Health Research Institute (Sun City, Ariz., USA). Pathological diagnosis of AD is made according to standard NIA-Reagan Institute criteria based on neuropathological data. The radioligand [$^3$H]T808 was synthesized in-house ([$^3$H]-2-[4-(2-Fluoro-ethyl)-piperidin-1-yl]-benzo[4,5]imidazo[1,2-a]pyrimidine, radiochemical purity 99.0%). As a reference cold T808 is used (2-[4-(2-Fluoro-ethyl)-piperidin-1-yl]-benzo[4,5]imidazo[1,2-a]pyrimidine). For the autoradiography FujiFilm Imaging Plates (BAS-IP TR 2025) are exposed to the sections and read with a FujiFilm IP reader (BAS-5000).

Method

Ten µm thick human AD brain sections are generated with a cryostat (Leica CM3050) at −17° C. chamber temperature and −15° C. object temperature. Sections are transferred to Histobond+ microscope slides (Marienfeld Laboratory Glasware). After drying for 3 hours at room temperature the sections are stored at −20° C. The sections are incubated with the radioligand (10 nM) and the respective cold compound (at various concentrations) in 50 mM Tris buffer, pH 7.4 at room temperature for 30 min. After washing 3×10 min at 4° C. in 50 mM Tris buffer, pH 7.4 and 3 quick dips in H$_2$O dist. at 4° C. the sections are dried at 4° C. for 3 h. The sections are placed in a FujiFilm Cassette (BAS 2025), exposed with an Imaging Plate for five days and afterwards scanned with a resolution of 25 µM per pixel.

Data Analysis

The signal intensity (Dens-PSL/mm2) in the region of interest (ROI) of the autoradiogram is quantified with the software MCID analysis (version 7.0, Imaging Research Inc.). The specific binding (SB) of [$^3$H]T808 binding in absence or in presence of a compound is calculated by subtracting the non-specific binding signal in the white matter, thus yielding $SB_{[3H]T808\ only}$ and $SB_{compound}$. The % displacement by the various compounds is calculated as following:

% displacement=100−($SB_{compound}$/$SB_{[3H]T808\ only}$) *100.

Validation Data

In each experiment cold T808 is used as a positive internal control. Co-incubation of equimolar amounts of hot and cold T808 is expected to reduce specific binding by approximately 50%.

REFERENCES

A. K. Szardenings et al. 'Imaging agents for detecting neurological disorders'. US Patent Application US20110182812

W. Zhang et al., 'A highly selective and specific PET tracer for imaging of tau pathologies'. *Journal of Alzheimer's Disease* 31 (2012) 601-612.

[1,2-a]pyridin-7-amine (example 6) incubated with human cortical brain sections obtained from a Braak V staged AD patient. The radioligand concentrations were 2.6 and 2.5 nM, respectively. Both radioligands show punctate staining of tau aggregates in a layered distribution pattern and a varying degree of non-specific binding in white matter.

The compounds of formula I and pharmaceutically acceptable salts thereof can be used in the form of pharmaceutical preparations. The pharmaceutical preparations can be administered in form of injection solutions.

The compounds of formula I and pharmaceutically acceptable salts thereof can be processed with pharmaceutically inert, inorganic or organic carriers for the production of pharmaceutical preparations. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for

TABLE 1

| Structure | Name | % displacement of [$^3$H]T808 (10 nM) at 10 nM | Example |
|---|---|---|---|
| 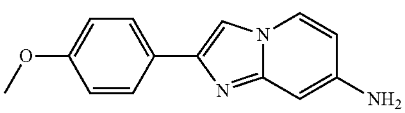 [SMILES: COc1ccc(-c2cn3ccc(N)cc3n2)cc1] | 2-(4-methoxyphenyl)imidazo[1,2-a]pyridin-7-amine | 67 | 1 |
| 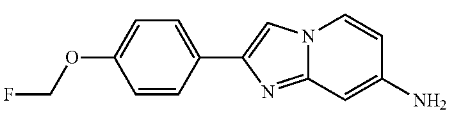 | 2-(4-(fluoromethoxy)phenyl)imidazo[1,2-a]pyridin-7-amine | 51 | 2 |
| 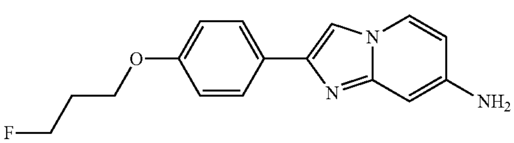 [SMILES: Nc1ccn2cc(-c3ccc(OCCCF)cc3)nc2c1] | 2-[4-(3-fluoropropoxy)phenyl]imidazo[1,2-a]pyridin-7-amine | 25 | 3 |
| 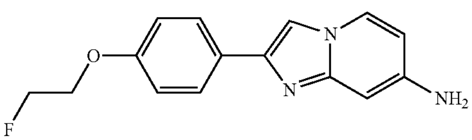 [SMILES: Nc1ccn2cc(-c3ccc(OCCF)cc3)nc2c1] | 2-[4-(2-fluoroethoxy)phenyl]imidazo[1,2-a]pyridin-7-amine | 50 | 4 |
| 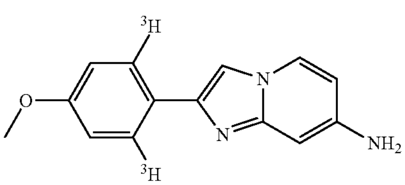 [SMILES: [3H]c1cc(OC)cc([3H])c1-c1cn2ccc(N)cc2n1] | [$^3$H]-2-(4-methoxyphenyl)imidazo[1,2-a]pyridin-7-amine |  | 5 |
| 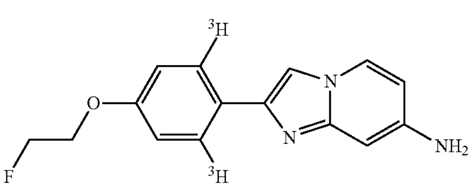 [SMILES: [3H]c1cc(OCCF)cc([3H])c1-c1cn2ccc(N)cc2n1] | [$^3$H]-2-[4-(2-fluoroethoxy)phenyl]imidazo[1,2-a]pyridin-7-amine |  | 6 |

FIGS. 1 and 2 represent autoradiograms of respectively [[$^3$H]-2-(4-methoxyphenyl)imidazo[1,2-a]pyridin-7-amine (example 5) and [$^3$H]-2-[4-(2-fluoroethoxy)phenyl]imidazo example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case.

EXAMPLES

Abbreviations Used h—hour(s)
min—minute(s)

Example 1

2-(4-Methoxyphenyl)imidazo[1,2-a]pyridin-7-amine

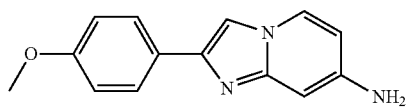

A microwave vial was charged with pyridine-2,4-diamine (400 mg, 3.67 mmol), 2-bromo-1-(4-methoxyphenyl)ethanone (882 mg, 3.85 mmol), sodium bicarbonate (329 mg, 3.92 mmol) and methanol (3.5 mL). The reaction mixture was stirred at reflux for 4 h. The reaction mixture was cooled to room temperature, diluted with water and ethyl acetate, sonicated and stirred at room temperature for ~15 min. The suspension was filtered, rinsed with water and ethyl acetate. The resulting pale yellow solid was put under high vacuum to afford 2-(4-methoxyphenyl)imidazo[1,2-a]pyridin-7-amine hydrobromide. It was suspended in ~5 mL saturated aqueous NaHCO$_3$-solution, sonicated, filtered and rinsed with water. The residue was suspended in ~5 mL aqueous 2M NaOH-solution, sonicated, filtered and rinsed with water. The resulting residue was put under high vacuum to afford the title compound as a light brown solid (310 mg, 1.3 mmol, 35% yield). MS m/z: 240.1 [M+H]$^+$.

Example 2

2-(4-(Fluoromethoxy)phenyl)imidazo[1,2-a]pyridin-7-amine

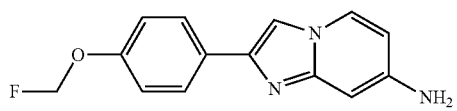 [SMILES: Nc1ccn2cc(-c3ccc(OCF)cc3)nc2c1]

a) 7-Bromo-2-(4-(hydroxyphenyl)imidazo[1,2-a]pyridine

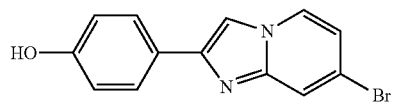

In analogy to example 1, 4-bromopyridin-2-amine instead of pyridine-2,4-diamine and 2-bromo-1-(4-hydroxyphenyl)ethanone instead of bromo-1-(4-methoxyphenyl)ethanone were converted into the title compound (2.34 g, 80%) which was obtained as a grey solid. MS m/z: 289.3 [M]$^+$.

b) 7-Bromo-2-(4-(fluoromethoxy)phenyl)imidazo[1,2-a]pyridine

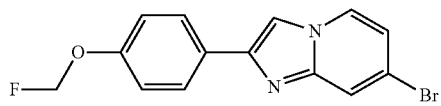 [SMILES: FCOc1ccc(-c2cn3ccc(Br)cc3n2)cc1]

To a solution of 4-(7-bromoimidazo[1,2-a]pyridin-2-yl)phenol (2.37 g, 6.56 mmol) and fluoromethyl 4-methylbenzenesulfonate (1.34 g, 6.56 mmol) in DMF (10.00 mL) was added cesium carbonate (2.78 g, 8.52 mmol) and heated to 70° C. for 18 h and then irradiated for 30 minutes at 100° C. in the microwave. It was poured into water and extracted two times with dichloromethane. The organic layers were combined, dried over sodium sulfate, filtrated and concentrated. To the resulting oil was added toluene (~200 mL) and the solvent was evaporated to remove the remaining DMF. Some NaOH$_{aq}$ 1 N was added and stirring was continued for 15 minutes. It was filtrated and dried at high vacuum affording the title compound (1.69 g, purity ~60%) as a light brown oil which was used without further purification. MS m/z: 321.3 [M+H]$^+$.

c) 2-(4-(Fluoromethoxy)phenyl)imidazo[1,2-a]pyridin-7-amine

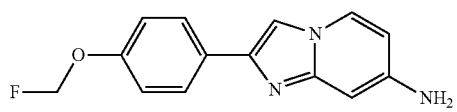

To a solution of 7-bromo-2-(4-(fluoromethoxy)phenyl)imidazo[1,2-a]pyridine (112 mg, 349 μmol) in N-methyl-2-pyrrolidinone (2 mL) was added copper(I) oxide (9.98 mg, 69.8 μmol) and ammonium hydroxide (733 mg, 5.23 mmol). Then the vial was closed and the reaction mixture was stirred at 110° C. for 3 h. It was diluted with dichloromethane (15 mL) and was washed twice with water (15 mL). The aqueous layers were extracted with dichloromethane (15 mL). The combined organic layers were dried over magnesium sulfate, filtered and concentrated. Flash chromatography using a dichloromethane:dichloromethane:methanol:ammonia (90:9:1 vol. %) gradient 85:15 to 50:50 afforded the title compound (17 mg, 19% yield) as a light brown solid. MS m/z: 258.6 [M+H]$^+$.

Example 3

2-[4-(3-Fluoropropoxy)phenyl]imidazo[1,2-a]pyridin-7-amine

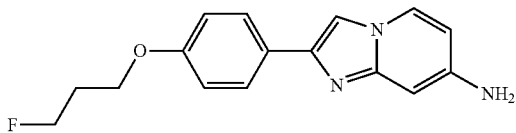 [SMILES: Nc1ccn2cc(-c3ccc(OCCCF)cc3)nc2c1]

a) 4-(7-Aminoimidazo[1,2-a]pyridin-2-yl)phenol hydrobromide

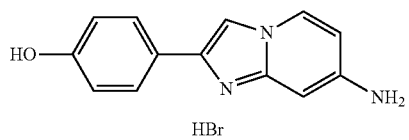 [SMILES: Nc1ccn2cc(-c3ccc(O)cc3)nc2c1 ; Br]

In a 5 mL microwave vial, pyridine-2,4-diamine (500 mg, 4.58 mmol) and 2-bromo-1-(4-hydroxyphenyl)ethanone (1.03 g, 4.81 mmol) were combined with acetone (8.0 mL) to give an off-white suspension. The vial was flushed with argon and closed. The reaction mixture was stirred at 65° C. (oil bath temperature) overnight. The off-white suspension was filtered and washed with acetone. The resulting off-white solid was dried under high vacuum overnight to afford the title compound (363 mg, 18% yield) as an off-white solid. MS m/z: 226.1 [M+H]$^+$.

b) 2-[4-(3-Fluoropropoxy)phenyl]imidazo[1,2-a]pyridin-7-amine

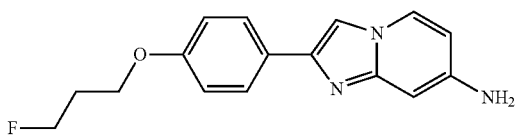

In a 5 mL microwave vial, 4-(7-aminoimidazo[1,2-a]pyridin-2-yl)phenol hydrobromide (150 mg, 343 µmol) was combined with DMF (2.5 mL) to give a colorless solution. Cesium carbonate (335 mg, 1.03 mmol) was added. The reaction mixture was stirred at room temperature for 1 h (gas evolution observed; the reaction mixture turned into a dark-brown suspension). 1-Bromo-3-fluoropropane (48.4 mg, 343 µmol) dissolved in DMF (0.5 mL) was added. The vial was flushed with argon and closed. The reaction mixture was stirred at 90° C. (oil bath temperature) overnight. The reaction mixture was cooled down to ambient temperature and extracted with dichloromethane and water. The aqueous layer (pH ~9) was extracted with dichloromethane. The organic layers were washed three times with water and once with brine. The organic layers were combined, dried over magnesium sulfate, filtered and concentrated. The residue (brown oil) was dried at high vacuum for 4 h. The brown solid was triturated with ethyl acetate to afford the title compound (53 mg, 48% yield) as a brown solid. MS m/z: 286.1 [M+H]$^+$.

Example 4

2-[4-(2-Fluoroethoxy)phenyl]imidazo[1,2-a]pyridin-7-amine

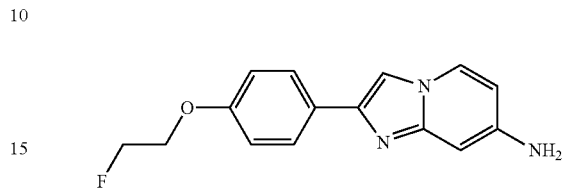

To a solution of 4-(7-aminoimidazo[1,2-a]pyridin-2-yl)phenol hydrobromide (156 mg, 510 µmol) in DMF (2 mL) was added under an atmosphere of nitrogen at 0° C. sodium hydride 60% (81.5 mg, 2.04 mmol). After stirring at ambient temperature for 30 min 1-bromo-2-fluoroethane (71.2 mg, 560 µmol) was added over a period of 1 min. Then the reaction mixture was stirred at ambient temperature for 2 h. It was poured on water (15 mL) and extracted twice with ethyl acetate (15 mL). The organic layers were washed with water (15 mL) and brine (10 mL). The combined organic layers were dried over magnesium sulfate, filtered and concentrated. Flash chromatography using a dichloromethane:dichloromethane:methanol:ammonia (90:9:1 vol. %) gradient 80:20 to 40:60 afforded the title compound (80 mg, 58% yield) as an off-white solid. MS m/z: 272.5 [M+H]$^+$.

Example 5

[$^3$H]-2-(4-Methoxyphenyl)imidazo[1,2-a]pyridin-7-amine

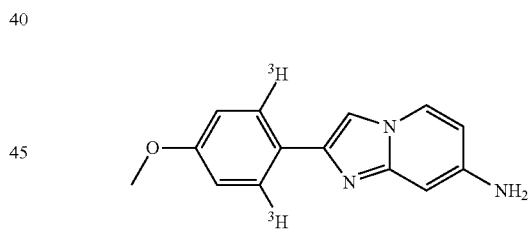

In a 2 mL tritiation flask, 2-(4-methoxyphenyl)imidazo[1,2-a]pyridin-7-amine (2.0 mg, 8.4 µmol) and Crabtree's catalyst (10.1 mg, 15.5 µmol) were dissolved in dichloromethane (1.0 mL). The flask was attached to the tritium manifold (RC-TRITEC) and degassed by freeze-pump-thaw. Tritium gas was introduced, and the light orange solution was vigorously stirred for 4 h in an atmosphere of tritium at 1050 mbar. The solution was cooled by liquid nitrogen and the excess tritium gas in the reaction vessel was reabsorbed on a uranium-trap for waste-tritium. The solvent was lyophilized off and labile tritium was removed by lyophilization with a 9:1-mixture of ethanol and water (3×1 mL) and toluene (2×1 mL). The remaining brownish oil was dissolved in dichloromethane (25 mL) and transferred on a SCX-3 cation exchanger. Remaining catalyst was eluted with dichloromethane (15 mL) and discarded, the product was eluted with NH$_3$ in MeOH (1 N, 25 mL), collected separately, and concentrated under reduced pressure. The crude product was purified by preparative HPLC (XBridge C-18 Prep, 5 μm, 10×250 mm) using acetonitrile, water, and pH 9 buffer as eluent. 833 MBq (22.5 mCi) were obtained of the title compound with a radiochemical purity of 99% and a specific activity of 1.02 TBq/mmol (27.6 Ci/mmol), as determined by MS spectrometry. The compound was stored as an ethanolic solution. MS m/z: 240.2 [M+H]$^+$ (48%), 242.2 [M(T)+H]$^+$ (10%), 244.2 [M(T$_2$)+H]$^+$ (40%), 246.2 [M(T$_3$)+H]$^+$ (2%).

Example 6

[$^3$H]-2-[4-(2-Fluoroethoxy)phenyl]imidazo[1,2-a]pyridin-7-amine

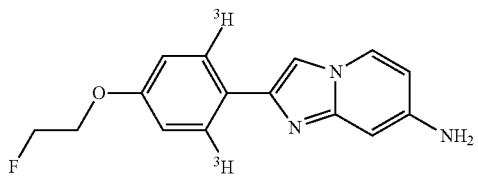 [SMILES: [3H]c1cc(OCCF)cc([3H])c1-c1cn2ccc(N)cc2n1]

In a 2 mL tritiation flask, 2-[4-(2-fluoroethoxy)phenyl]imidazo[1,2-a]pyridin-7-amine (2.0 mg, 7.4 μmol) and Crabtree's catalyst (5.9 mg, 7.4 μmol) were dissolved in DMF (1.0 mL). The flask was attached to the tritium manifold (RC-TRITEC) and degassed by freeze-pump-thaw. Tritium gas was introduced, and the light orange solution was vigorously stirred for 4 h in an atmosphere of tritium at 550 mbar. The solution was cooled by liquid nitrogen and the excess tritium gas in the reaction vessel was reabsorbed on a uranium-trap for waste-tritium. The solvent was lyophilized off and labile tritium was removed by lyophilization with a 9:1-mixture of ethanol and water (3×1 mL) and toluene (2×1 mL). The remaining brownish oil was dissolved in dichloromethane (10 mL) and transferred on a SCX-3 cation exchanger. Remaining catalyst was eluted with MeOH (5 mL) and discarded, the product was eluted with NH$_3$ in MeOH (3.5 N, 5 mL) and MeOH (35 mL), collected separately, and concentrated under reduced pressure. The crude product was purified by preparative HPLC (XBridge C-18 Prep, 5 μm, 10×250 mm) using acetonitrile, water, and pH 7 buffer as eluent. 833 MBq (22.5 mCi) were obtained of the title compound with a radiochemical purity of 98% and a specific activity of 1.58 TBq/mmol (42.6 Ci/mmol), as determined by MS spectrometry. The compound was stored as a methanolic solution. MS m/z: 272.2 [M+H]$^+$ (7%), 274.2 [M(T)+H]$^+$ (39%), 276.2 [M(T$_2$)+H]$^+$ (54%).

The invention claimed is:
1. A compound of Formula I

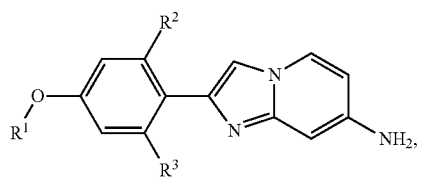

Formula I wherein

R$^1$ is lower alkyl or lower alkyl substituted by halogen;
R$^2$, R$^3$ are hydrogen or tritium;
or a pharmaceutically acceptable acid addition salt thereof.

2. The compound of Formula I according to claim 1, wherein R$^1$ is lower alkyl and R$^2$ and R$^3$ are as described in claim 1.

3. The compound of Formula I according to claim 1, which is
2-(4-methoxyphenyl)imidazo[1,2-a]pyridin-7-amine or
[$^3$H]-2-(4-methoxyphenyl)imidazo[1,2-a]pyridin-7-amine.

4. The compound of Formula I according to claim 1, wherein R$^1$ is lower alkyl substituted by halogen and R$^2$ and R$^3$ are as described in claim 1.

5. The compound of Formula I according to claim 1, which compound is
2-(4-(fluoromethoxy)phenyl)imidazo[1,2-a]pyridin-7-amine,
2-[4-(3-fluoropropoxy)phenyl]imidazo[1,2-a]pyridin-7-amine,
2-[4-(2-fluoroethoxy)phenyl]imidazo[1,2-a]pyridin-7-amine, or
[$^3$H]-2-[4-(2-fluoroethoxy)phenyl]imidazo[1,2-a]pyridin-7-amine.

6. The compound of Formula I according to claim 1, wherein R$^2$ and R$^3$ are tritium and R$^1$ is as described in claim 1.

7. The compound of Formula I according to claim 1, which compound is
[$^3$H]-2-(4-methoxyphenyl)imidazo[1,2-a]pyridin-7-amine or
[$^3$H]-2-[4-(2-fluoroethoxy)phenyl]imidazo[1,2-a]pyridin-7-amine.

8. A process for the manufacture of a compound of Formula I as defined in claim 1, which process comprises one of the following a)-d)
a) amination of a compound of Formula 2 (X=Cl, Br)

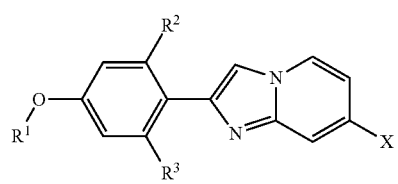

Formula 2 wherein R$^1$ is as in claim 1, and R$^2$ and R$^3$ are each hydrogen, with NH$_4$OH,
thus producing the following compound of Formula I, called Compound A

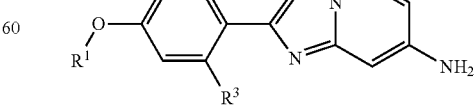

Compound A wherein R$^1$ is as defined in claim 1, and R$^2$ and R$^3$ are hydrogen, and, optionally, converting Compound A into a pharmaceutically acceptable acid addition salt, or b) coupling a compound of Formula 4

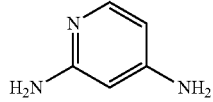

Formula 4 with a corresponding α-activated ketone of Formula 3 (X is a leaving group)

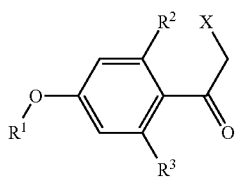

Formula 3 wherein $R^1$ is as in claim 1, and $R^2$ and $R^3$ are each hydrogen, thus producing Compound A of Formula I

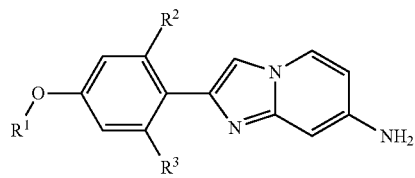

Compound A wherein $R^1$ is as defined in claim 1, and $R^2$ and $R^3$ are hydrogen, and, optionally, converting the compound obtained into a pharmaceutically acceptable acid addition salt, or c) reacting a compound of Formula 5

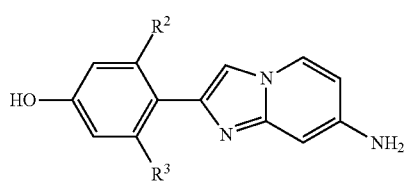

Formula 5 wherein $R^2$ and $R^3$ are each hydrogen, with a alkylation agent $R^1$—X (X is halogen or sulfonate) thus producing the following compound of Formula I, called Compound B

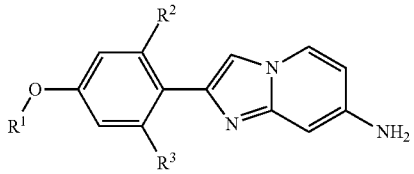

Compound B wherein $R^1$ is as defined in claim 1, and $R^2$ and $R^3$ are hydrogen, and, optionally, converting Compound B into a pharmaceutically acceptable acid addition salt, or d) reacting Compound C

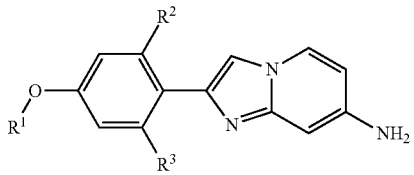

Compound C wherein $R^1$ is as in claim 1, and $R^2$ and $R^3$ are hydrogen, with tritium gas in the presence of a catalyst selected from the group consisting of iridium, ruthenium, rhodium and palladium containing complexes, in a solvent selected from the group consisting of dichloromethane, chlorobenzene, DMF, and DMSO or mixtures thereof, thus producing the following compound of Formula I, called Compound D

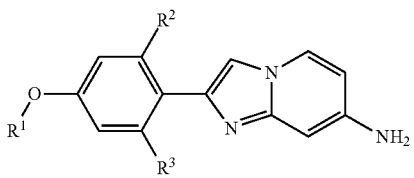

Compound D wherein $R^1$ is as defined in claim 1 and $R^2$ and $R^3$ are tritium, and, optionally, converting the compound obtained into a pharmaceutically acceptable acid addition salt.

9. A pharmaceutical composition comprising a compound of Formula I according to claim 1, and a pharmaceutical acceptable carrier.

10. A method of imaging tau-aggregate deposits, beta-amyloid aggregate deposits, or alpha-synuclein aggregate deposits, comprising
  introducing into a mammal a detectable quantity of the composition according claim 9; and
  detecting the compound bound to one or more deposits selected from tau-aggregate, beta-amyloid aggregate, or alpha-synuclein aggregate via diagnostic imaging.

11. The method of claim 10, wherein the deposits are tau-aggregate deposits.

* * * * *